United States Patent [19]

Suzaki et al.

[11] Patent Number: 4,773,097
[45] Date of Patent: Sep. 20, 1988

[54] IMAGE ANALYZING APPARATUS

[75] Inventors: Takuji Suzaki; Koji Yamamoto; Satoko Nakajima, all of Kyoto, Japan

[73] Assignee: Omron Tateisi Electronics Co., Japan

[21] Appl. No.: 40,770

[22] Filed: Apr. 20, 1987

Related U.S. Application Data

[63] Continuation of Ser. No. 704,688, Feb. 22, 1985, abandoned.

[30] Foreign Application Priority Data

May 31, 1984 [JP] Japan ............... 59-112593

[51] Int. Cl.$^4$ .............................................. G06K 9/00
[52] U.S. Cl. ........................................ 382/6; 382/1; 128/633; 128/634; 128/665; 250/461.2; 356/39; 356/41; 364/413.02; 364/413.09
[58] Field of Search ............... 128/633, 634, 664, 665; 250/461.2; 350/320, 418; 356/39–41; 364/416; 382/1, 6, 39, 69

[56] References Cited

U.S. PATENT DOCUMENTS

| | | | |
|---|---|---|---|
| 4,170,987 | 10/1979 | Anselmo et al. | 128/665 |
| 4,178,917 | 12/1979 | Shapiro | 128/665 |
| 4,194,217 | 3/1980 | van den Bosch | 128/633 |
| 4,213,462 | 7/1980 | Sato | 128/634 |
| 4,505,583 | 3/1985 | Konomi | 356/73 |
| 4,513,751 | 4/1985 | Abe et al. | 128/633 |
| 4,573,195 | 2/1986 | de France | 382/6 |
| 4,622,291 | 11/1986 | Picciolo et al. | 436/46 |
| 4,627,014 | 12/1986 | Lo et al. | 436/97 |

FOREIGN PATENT DOCUMENTS 55-46726  11/1980  Japan.

Primary Examiner—Leo H. Boudreau
Assistant Examiner—Jose L. Couso
Attorney, Agent, or Firm—Wegner & Bretschneider

[57] ABSTRACT

An image analyzing apparatus comprising a source of light for radiating a target object of interest, a measuring light of a first predetermined wavelength and at least one detecting light of a second predetermined wavelength different from the first predetermined wavelength, which detecting light is utilized to detect an optically disturbing component, a camera unit for forming a measured image of the target object radiated by the measuring light and a detected image of the target object radiated by the detecting light, and capable of generating output signals representative of the respective measured and detected images, a processor for deriving an interference equation descriptive of an interference given by the optically disturbing component, on the basis of the measured and detected images outputed from the camera unit, a computer for eliminating the optically disturbing component from the measured image on the basis of the interference equation, and a display device for providing a visual representation of an image output from the computer.

4 Claims, 3 Drawing Sheets

IMAGE ANALYZING APPARATUS

This application is a continuation of U.S. application Ser. No. 704,688, filed Feb. 22, 1985, now abandoned.

BACKGROUND OF THE INVENTION

The present invention generally relates to an image analyzing apparatus for analyzing an image by radiating a target object to be analyzed such as living tissues or organs and, more particularly, to an apparatus for the fluorometric analysis.

As is well known to those skilled in the art, the oxidation-reduction (oxidoreduction) of pyridine-nucleotide present in the living tissue or organ such as NADH (reduced nicotinamide adenine dinucleotide) and NADPH (reduced nicotinamide adenine dinucleotide phosphate), which pyridine-nucleotide is hereinafter referred to as "PN", provides an indication of the state of respiratory function (metabolism) of the living tissue. The reduced PN has a property of emitting fluorescence when excited by ultraviolet radiation. Therefore, by analyzing the oxidoreduction of the PN through the fluorometric technique, the state of respiratory metabolism of the living tissue can be monitored. Moreover, if the fluorescence emission from the PN is analyzed in two-dimensional geometry, the affected locality of the living tissue at which abnormal respiratory metabolism takes place can be located.

However, it has been found that, during the clinical examination of the PN fluorescence image, the presence of blood in the living tissue being examined provides an optical interference to the fluorescence emission. In other words, since the blood shows an absorption band within a spectrum of wavelengths of the fluorescence emission from the PN, the intervention of the blood brings an undesirable optical interference on the PN fluorescence emission with the consequence that the more fluorescence emission tends to be indicated when the blood content is small at a given locality of the living tissue than when it is great at the same locality. Therefore, the optical interference brought about by the intervention of the blood must be compensated for in order to avoid such a false indication.

In view of the foregoing, the assignee of the present invention has disclosed, by way of the Japanese Patent Publication No. 55-46726, published Nov. 26, 1980, a method for the compensation for the optical interference to the PN fluorescence emission resulting from fluctuations in blood content in the living tissue. According to this publication, the application of the compensating method to determine the accurate fluorescence emission from the PN in the living tissue requires the use of an interference equation descriptive of the optical interference, which equation was derived from the relationship between the fluorescence emission, resulting from the radiation of exciting light, and the amount of reference light radiated onto and then reflected from the living tissue.

In establishing the interference equation according to the above mentioned publication, however, the prior art method requires the use of a living tissue different from the living tissue of interest. This means that not only can the interference equation so derived be not regarded as applicable universally to all living tissues, but also the interference equation so derived requires adjustment depending on the optical conditions. Therefore, it has been found that the clinical use of the interference equation descriptive of the interference brings about no practical result.

SUMMARY OF THE INVENTION

The present invention has been developed with a view to substantially eliminating the disadvantages and inconveniences inherent in the prior art method and apparatus and has for its essential object to provide an improved image analyzing apparatus wherein image information derived from a target object of interest is utilized to give an interference equation descriptive of the optical interference, which equation is in turn used to correct the image information on the target object of interest so that an image of the measured light can be displayed on a real time basis.

In order to accomplish this object, an image analyzing apparatus herein disclosed according to the present invention broadly comprises a source of light for radiating a target object of interest, a measuring light of a first predetermined wavelength and at least one detecting light of a second predetermined wavelength different from the first predetermined wavelength, said detecting light being utilized to detect an optically disturbing component; an image forming means for forming a measured image of the target object radiated by the measuring light and a detected image of the target object radiated by the detecting light, and capable of generating output signals representative of said respective measured and detected images; means for deriving an interference equation descriptive of an interference given by the optically disturbing component, on the basis of the measured and detected images outputed from the image forming means; a processor means for eliminating the optically disturbing component from the measured image on the basis of the interference equation; and a display means for providing a visual representation of an image output from the processor means.

With the image analyzing apparatus according to the present invention, since the interference equation is derived by directly radiating the target object of interest with both of the measuring light and the detecting light, compensation can be automatically performed to provide an actually measured image on real time basis and, therefore, the image analysis can be accurately and readily performed.

By way of example, with the apparatus according to the present invention, the actual fluorescence emission and the pattern of distribution of fluorescences of the PN in the vital organ can be monitored for the accurate determination of the state of respiratory metabolism of the vital organ. In particular, the apparatus according to the present invention is suited for the determination of the affected locality, and the condition, of at least one functional abnormality of a vital organ resulting from one or more ischemic syndromes such as, for example, cerebral infarction, cerebral thrmbosis and myocardial infarction, or from trauma due to, for example, a traffic accident, or from the administration of drugs and/or injection.

BRIEF DESCRIPTION OF THE DRAWINGS

This and other objects and features of the present invention will become readily understood from the following detailed description of some preferred embodiments of the present invention made with reference to the accompanying drawings, in which:

FIG. 4 is a schematic plan view showing a different form of a rotary filter which can be employed in the practice of the present invention.

DETAILED DESCRIPTION OF THE EMBODIMENTS

Figure 1:
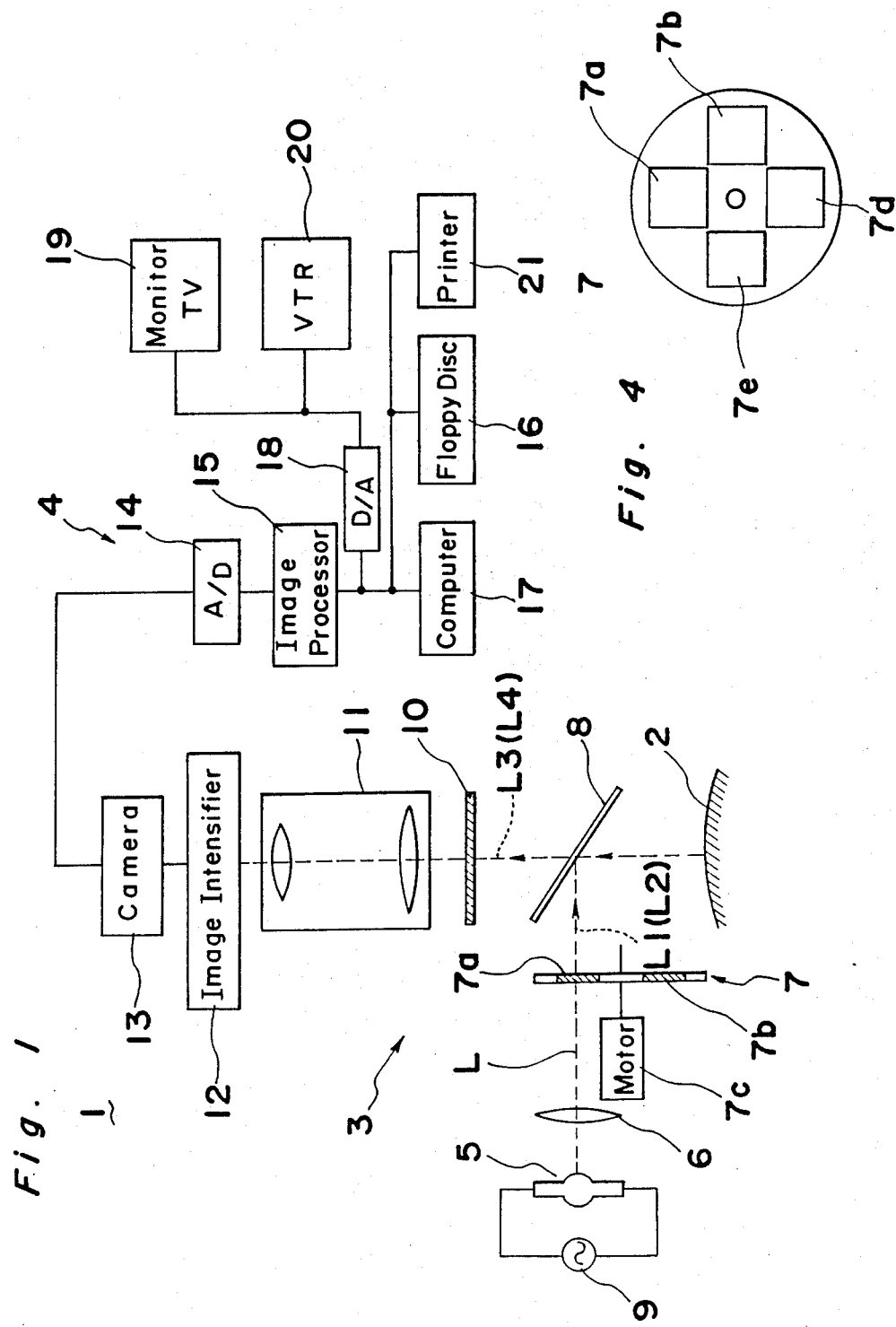
FIG. 1 is a schematic circuit block diagram showing an image analyzing apparatus according to a first preferred embodiment of the present invention.

Before the description of the present invention proceeds, it is to be noted that like parts are designated by like reference numerals throughout the accompanying drawings.

The principle of the image analysis of a living organ which embodies the present invention will first be described.

When exciting light (measuring light) of 360 nm in wavelength is radiated on a living organ, fluorescence of 450 to 480 nm in wavelength is emitted from the reduced PN contained in the living organ. However, the fluorescence emission is in most cases adversely affected by an optical medium such as, for example, the background light reflected from cells in a surface layer of the living organ and/or the content of blood flowing in the living tissue. Accordingly, the amount of fluorescence measured will be of a value equal to a difference between the amount of fluorescence attributable to the oxidoreduction of the PN being examined and the amount of fluorescence given by fluctuations of the blood content.

In view of the above, in the practice of the present invention, the exciting light (measuring light) and the reference light (detecting light) are either simultaneously or separately radiated towards the living organ to be examined. When this reference light is radiated, the intensity of the reference light which has been reflected and then scattered by the living organ varies, in a manner similar to the fluorescence emission, with changes in blood content and/or changes in parameter of the optical measuring system and provides information attributable to apparent variables (disturbing component).

An interference equation descriptive of the interference given by the changes in blood content can be derived by the utilization of the information attributable to the apparent variables. In other words, a fluorescence image of the living organ (measured image) presented by the fluorescence emission and a reflectance image (detected image) of the living organ presented by the reference light are formed by a camera and are then compared with each other so that the extent of interference, brought about by the blood content, can be determined on the basis of changes in intensity of the fluorescence emission and the reflected reference light to derive the interference equation. By the use of this interference equation, a signal representative of the fluorescence image is processed to eliminate the disturbing component which represents the apparent variables, thereby giving the actual amount of fluorescence emitted from the PN. Making reference to the fluorescence image, the pattern of distribution of active substances participating in the metabolism of the living organ can be determined.

Specific embodiments of the present invention based on the above described principle will now be described with reference to FIGS. 1 to 5.

Referring particularly to FIG. 1, there is shown an image analyzing apparatus, generally identified by 1, according to a first preferred embodiment of the present invention. This apparatus 1 generally comprises an optical system 3 and a signal processing system 4. The optical system 3 is so designed as to radiate light towards a living organ 2 to produce image information and includes a source 5 of light for emitting a beam L of light for illuminating the living organ 2. The light beam L emitted from the light source 5 travels towards a semi-transparent mirror 8 through a lens 6 and then through a rotary filter 7 (filtering means) and is then radiated to the living organ 2 after having been reflected from the semi-transparent mirror 8.

The light source 5 is electrically connected with a source 9 of electrical power. The rotary filter unit 7 includes two interference filters 7a and 7b and is drivingly coupled with an electric motor 7c (switching means). The first filter 7a is adapted to pass therethrough a beam of light of 360 nm in wavelength which serves as an exciting light L1 for illuminating the living organ 2. On the other hand, the second filter 7b is adapted to pass therethrough a beam of light of 420 nm in wavelength which serves as a reference light L2 for illuminating the living organ 2.

When the living organ 2 is radiated by the exciting light L1, fluorescence L3 of 450 to 480 nm in wavelength can be emitted from the living organ 2. This fluorescence L3 is subsequently transmitted, together with a component L4 of the reference light L2 which has been reflected from the living organ 2, to a camera unit 13 of the signal processing system 4 through a filter 10, then a microscope 11 and finally an image intensifier 12.

The camera unit 13 in the embodiment shown in FIG. 1 comprises a single camera and has an image receiving surface on which a fluorescence image and a reflectance image of the living organ 2 can be formed. Image output signals emerging from this camera unit 13 are converted by an analog-to-digital converter 14 into respective digital signals which are subsequently fed through an image processing device 15 to a floppy disc 16 for the storage thereof.

Both the image processing device 15 and the drive motor 7c are controlled by a computer 17. This computer 17 (deriving means) is so designed as to derive an interference equation based on the fluorescence image and the reflectance image. An output from the computer 17 indicative of the interference equation is then supplied to the image processing device 15 whereupon the image processing device 15 (processing means) performs a processing of the fluorescence image according to the interference equation to eliminate a disturbing component and then generate an image output.

The image output emerging from the processing device 15 is, thereafter, converted by a digital-to-analog converter 18 into an analog signal which is subsequently displayed by a monitor televisio set 19 (display means), recorded in a video tape recorder 20 and/or printed out by a printer 21 (display means).

Hereinafter, the operation of the image analyzing apparatus 1 and a method for compensating for the optical interference will be described.

The light L emitted from the light source 5 is passed through the lens 6 and then through the rotary filter unit 7. The rotary filter 7 is rotated by the motor 7c under the control of the computer 17 so that the first and second interference filters 7a and 7b can be cyclically brought into the path of travel of the light L at an interval of, for example, 1/30 second, whereby the exciting light L1 of 360 nm in wavelength and the reference light L2 of 460 nm in wavelength can be selectively produced by the rotary filter unit 7 and then transmitted to the living organ 2 through the semi-transparent mirror 8.

Upon the radiation of the exciting light L1, the fluorescence L3 of 460 nm in wavelength is emitted from the living organ 2 and, on the other hand, the reference light L 2 is reflected, as the reflected light L4, from the living body 2. Both of the fluorescence L3 and the reflected light L4 contain a disturbing component attributable to the optical interference from fluctuations in blood content and are received by the camera unit 13 after having passed through the semi-transparent mirror 8, the filter 10, the microscope 11 and the image intensifier 12.

The fluorescence image and the reflectance image of the living organ 2 being examined are formed by the camera unit 13 on a time shared basis. The respective image output signals successively emerging from the camera unit 13 are converted by the analog-to-digital converter 14 into respective analog signals which are then stored in the floppy disc 16 through the image processing device 15.

Figure 2:
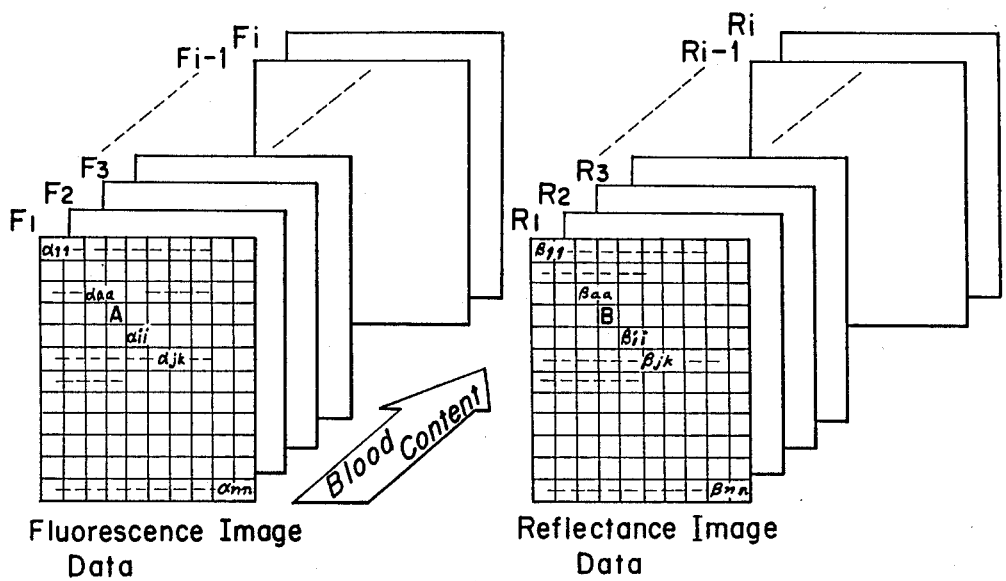
FIG. 2 is a schematic diagram showing both a fluorescence image data and a reflectance image data obtained from a living organ.
Figure 3:
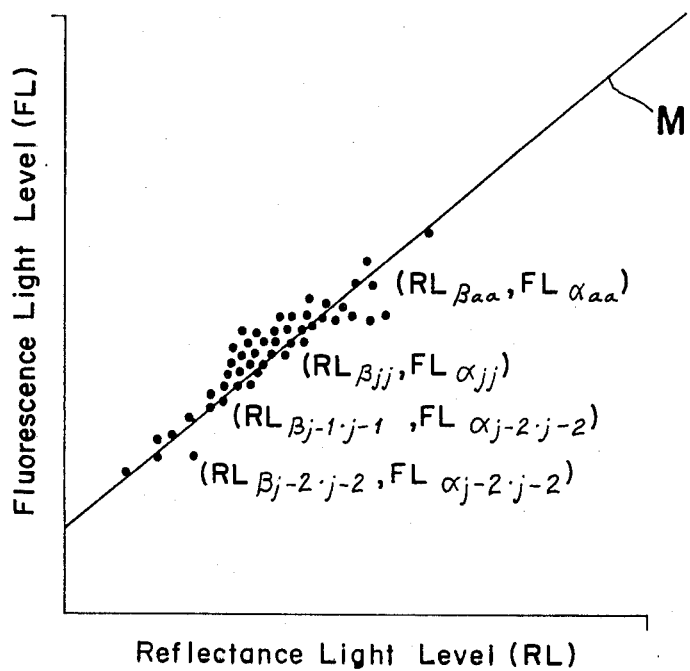
FIG. 3 is a graph showing the relationship between the amount of fluorescence emitted and the amount of light reflected.

By way of example, as shown in FIG. 2, paired data of the fluorescence and reflectance images are recorded in each of the associated files F1, F2, . . . Fi−1 and Fi and R1, R2, . . . Ri−1 and Ri. Based on the paired data of the respective files F1 and R1, the computer 17 samples out a location A, where the actual fluorescence L3 emitted from the PN is deemed to be uniform, and also a location B of the reflectance image, which corresponds to the location A, and then plots per address of the address locations (1, 2, . . . n;n·n=160×160)$\alpha_{aa} \sim \alpha_{jj}$, $\beta_{aa} \sim \beta_{jj}$ as shown in FIG. 3. In other words, the interference equation ($y=ax+b$) is derived by determining the correlation between the addresses $\alpha_{aa} \sim \alpha_{jj}$, $\beta_{aa} \sim \beta_{jj}$ from the graph wherein the axis of abscissas represents the light level (RL) of the reflected light L4 and the axis of ordinates represents the light level (FL) of the fluorescence L3, and then providing a regression line M to give the interference equation.

Based on the interference equation so derived, the image processing device 15 processes each pixel of the fluorescence image (for example, the file F1) to eliminate the disturbing component thereby forming the actual PN fluorescence image containing no optical interference from fluctuations in blood content. Then, for each fluorescene image, the interference equation is produced and calculated by the utilization of the files R1, R2, . . . Rn−1 and Rn which are different from each other and paired with the respective files F1, F2, . . . Fn−1 and Fn.

Thereafter, the actual fluorescence image data outputed from the image processing device 15 is, after having been converted by the digital-to-analog converter 18 into the analog signal, displayed by the monitor television set 19. Simultaneously with the display through the monitor television set 19, it may be recorded in the video tape recorder 20 and/or printed out by the printer 21.

In this way, when a brain, a liver or a kidney of, for example, an animal (rat, rabbit or the like) is examined by the utilization of the compensated PN fluorescence image, only the locality at which an ischemic syndrome is observed can be displayed in the form of a bright image and, accordingly, the presence of a pathological abnormality at which the respiratory function of the tissue is insufficient can readily be indicated.

Although in the foregoing embodiment the filter unit 7 has been described as including the two interference filters 7a and 7b, the number of the interference filters may not be limited to two such as shown, but may be three or more. So far shown in FIG. 4, the filter unit includes four interference filters 7a, 7b, 7d and 7e which are utilized not only for the purpose of producing the exciting and reference light L3 and L4 of 360 nm and 460 nm in wavelength, respectively, but also for the purpose of producing some other reference light of different wavelength necessary to eliminate disturbing components resulting from indentations present in the living organ 2. The filters 7a, 7b, 7d and 7e can be selectively brought into operation depending upon the purpose for which the image analysis is carried out. In any event, the number of the interference filters can be selected depending on the particular application.

Figure 5:
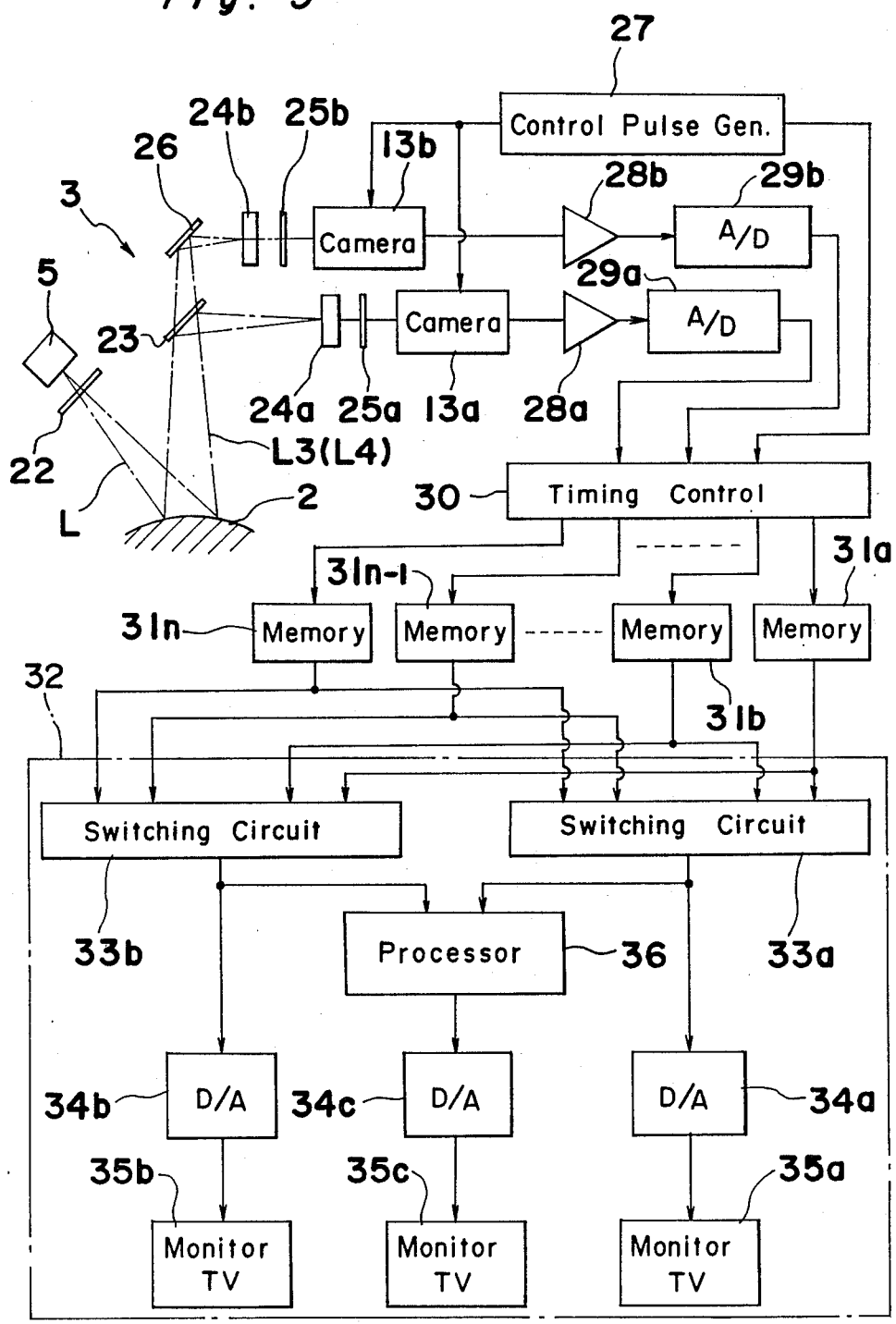
FIG. 5 is a schematic circuit block diagram showing the image analyzing apparatus according to another preferred embodiment of the present invention.

Referring now to FIG. 5 which illustrates the image analyzing apparatus according to another preferred embodiment of the present invention, the camera unit employed therein comprises first and second cameras 13a and 13b, in contrast to the single camera employed in the foregoing embodiment.

In the embodiment shown in FIG. 5, the light beam L emitted from the light source 5 is separated by a filter unit 22 into the exciting light L1 and the reference light L2 before it impinges upon the living organ 2. The resultant fluorescence L3 and the reflected light L4 are splited into two components by a semi-transparent mirror 23, the light component reflected by the semi-transparent mirror 23 being projected onto the first camera 13a through a lens 24a and then a first optical filter 25a while the light component passing through the semi-transparent mirror 23 is projected onto a reflective mirror 26 and is in turn projected onto the second camera 13b through a lens 24b and then a second optical filter 25b.

The first and second optical filters 25a and 25b are of a type capable of passing the fluorescence L3 and the reflected light L4, respectively. Therefore, it will readily be understood that the fluorescence image and the reflectance image are formed on image receiving surfaces of the first and second cameras 13a and 13b, respectively. The cameras 13a and 13b scan the respective images on the strength of vertical and horizontal video signals fed thereto from a control pulse generator 27 and output respective image output signals which are, after having been amplified by associated amplifier 28a and 28b and then converted by associated analog-to-digital converter 29a and 29b into digital image signals, fed to a switching timing control circuit 30.

The switching timing control circuit 30 operates selectively in response to the vertical and horizontal video signals, fed from the control pulse generator 27, and the fluorescence image and the reflectance image are, after having stored as one frame in memories 31a, 31b, ... 31n−1 and 31n, inputed to an image processing device 32. The image processing device 32 comprises first and second memory switching circuits 33a and 33b to which image output signals emerging from the respective memories 31a, 31b, ... 31n−1 and 31n are supplied. Image signals emerging respectively from the memory switching circuits 33a and 33b are, after having been converted by associated digital-to-analog converter 34a and 34b into analog image signals, fed to monitor television sets 35a and 35b for the visual presentation of the fluorescence image and the reflectance image, respectively. Simultaneously therewith, the image signals emerging from the memory switching circuits 33a and 33b, respectively, are fed to a processor 36 at which a required calculation is performed, an output from said processor 36 being, after having been converted by a digital-to-analog converter 34c into an analog image signal, fed to a monitor television set 35c for the visual presentation of the compensated fluorescence image and the reflectance image.

As hereinabove described, after the fluorescence image and the reflectance image of the living organ 2 have been formed by the separate cameras 13a and 13b, they are stored in the memories 31a, 31b, ... 31n−1 and 31n. The interference equation can be derived by the image processing device 32 in a manner similar to that described in connection with the foregoing embodiment shown in and described with reference to FIGS. 1 to 3.

It is to be noted that, although the camera unit in the embodiment shown in and described with reference to FIG. 5 has been described as comprising the two cameras, three or more cameras may be employed therefor depending on the number of the reference lights employed.

Although the present invention has fully been described in connection with the preferred embodiments thereof with reference to the accompanying drawings, it is to be noted that various changes and modifications are apparent to those skilled in the art. By way of example, the concept of the present invention can be equally applicable to a remote sensing system so designed as to make a topographical search to find an earth resource, for example, a forestry resource, by radiating rays of lights (electromagnetic waves) of different wavelength to the earth from a remote-sensing satellite. Where the forestry resource on the earth is desired to be remote-sensed by the use of red rays of light are employed, the presence of clouds between the earth and the remote-sensing satellite will provide an undesirable optical interference and, therefore, the employment of the reference light such as described in connection with the preferred embodiments of the present invention will be effective to ultimately compensate for the optical interference attributable to the clouds thereby providing a red-color image of the geographical area being sensed.

Moreover, the number of the detecting light may not be limited to one such as in the embodiments of the present invention, but may be determined according to the number of the disturbing components to be eliminated. Also, although reference has been made to the particular wavelengths for the exciting light L1 and the reference light L2, the wavelengths may not be always limited thereto and, hence, the interference equation may not be always limited to such as described in connection with the preferred embodiments of the present invention.

Furthermore, particularly in the embodiment of the present invention shown in and described with reference to FIGS. 1 to 3, each of the microscope 11 and the image intensifier 12 may be of a type comprising a single lens.

Accordingly, such changes and modifications are to be understood as included within the scope of the present invention as defined by the appended claims, unless they depart therefrom.

We claim:

1. An image analyzing apparatus, comprising:
    a source of light for radiating a target object of interest;
    a measuring light of a first predetermined wavelength and at least one detecting light of a second predetermined wavelength different from the first predetermined wavelength, said detecting light being utilized to detect an optically disturbing component;
    an image forming means for forming on an image receiving surface of at least one camera means a measured image of the target object radiated by the measuring light and a detected image of the target object radiated by the detecting light, and for generating output signals representative of said respective measured and detected images;
    means for deriving an interference equation descriptive of an interference given by the optically disturbing component, on the basis of the measured and detected images from the image forming means which automatically and dynamically provides a regression line as a function of each set of measured and detected images;
    a processor means for eliminating the optically disturbing component from the measured image on the basis of the interference equation; and
    a display means for providing a visual representation of an image output from the processor means.

2. An apparatus as claimed in claim 1, wherein said image forming means comprises a filtering means for selectively filtering the measuring light and the detecting light, a switching means operable to effect a switching of the filtering means, and a camera for forming the measured image and the detected image therein.

3. An apparatus as claimed in claim 1, wherein said image forming means comprises a filtering means for selectively filtering the measuring light and the detecting light, a switching means operable to effect a switching of the filtering means, and at least two cameras each for forming the measured image and the detected image.

4. The image analyzing apparatus as in claim 1, wherein said measuring and detecting lights radiate on the same target object of interest.

* * * * *